(12) United States Patent
Li et al.

(10) Patent No.: US 8,030,323 B2
(45) Date of Patent: Oct. 4, 2011

(54) PYRAZOLE CARBOXAMIDE DERIVATIVES, PHARMACEUTICAL COMPOSITIONS AND ITS PREPARATION

(75) Inventors: Song Li, Beijing (CN); Mengjia Liu, Beijing (CN); Zhibing Zheng, Beijing (CN)

(73) Assignee: Beijing Molecule Science and Technology Co., Ltd., Beijing (CN)

( * ) Notice: Subject to any disclaimer, the term of this patent is extended or adjusted under 35 U.S.C. 154(b) by 521 days.

(21) Appl. No.: 12/160,579

(22) PCT Filed: Jan. 10, 2007

(86) PCT No.: PCT/CN2007/000084
§ 371 (c)(1),
(2), (4) Date: Nov. 10, 2008

(87) PCT Pub. No.: WO2007/079681
PCT Pub. Date: Jul. 19, 2007

(65) Prior Publication Data
US 2010/0160383 A1    Jun. 24, 2010

(30) Foreign Application Priority Data
Jan. 11, 2006  (CN) .......................... 2006 1 0000730

(51) Int. Cl.
*A01N 43/40* (2006.01)
*A01N 43/42* (2006.01)
*A01N 43/56* (2006.01)
*A61K 31/435* (2006.01)
*A61K 31/44* (2006.01)
*A61K 31/415* (2006.01)

(52) U.S. Cl. ........ 514/277; 514/279; 514/336; 514/337; 514/338; 514/403; 514/406

(58) Field of Classification Search ........... 514/277, 514/279, 336, 337, 338, 403, 406
See application file for complete search history.

(56) References Cited

U.S. PATENT DOCUMENTS

| 5,462,960 A | 10/1995 | Barth et al. |
| 6,432,984 B1 | 8/2002 | Barth et al. |
| 6,509,367 B1 | 1/2003 | Martin et al. |

FOREIGN PATENT DOCUMENTS

| CA | 2 136 893 C | 6/2002 |
| WO | 03/088968 A1 | 10/2003 |

OTHER PUBLICATIONS

European Patent Office, Extended European Search Report for 0770216.2-2117/1975168 PCT/CN2007/000084, Jul. 22, 2010, Munich, Germany.

*Primary Examiner* — Yong Chong
(74) *Attorney, Agent, or Firm* — Kelly Lowry & Kelley, LLP

(57) ABSTRACT

A compound of formula (I) or pharmaceutically acceptable salts and/or solvates or hydrates thereof. A process for preparing the compound, a pharmaceutical composition comprising the compound and an application for resisting cannabinoid CB1 receptor are provided.

(I)

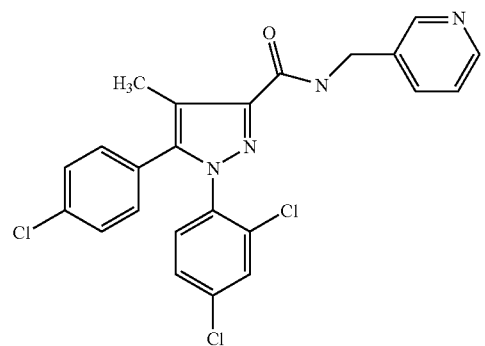

2 Claims, No Drawings

PYRAZOLE CARBOXAMIDE DERIVATIVES, PHARMACEUTICAL COMPOSITIONS AND ITS PREPARATION

The present invention relates to a compound of formula (I) and pharmaceutically acceptable salts and/or solvates or hydrates thereof, a process for preparing the compound, a pharmaceutical composition comprising the compound and its use for resisting cannabinoid CBI receptor.

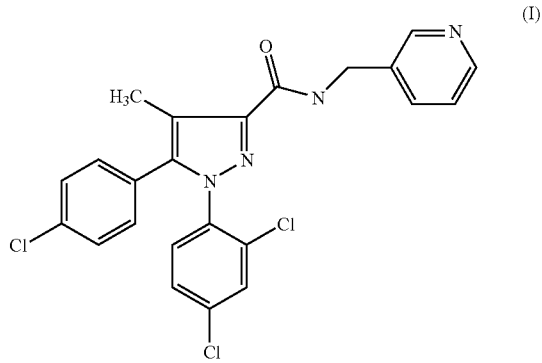

TECHNICAL FIELD

The present invention relates to pyrazole carboxamide derivatives of formula (I) and pharmaceutically acceptable salts and/or solvates or hydrates thereof, a process for preparing the compound, a pharmaceutical composition comprising the compound and its use for resisting cannabinoid CBI receptor.

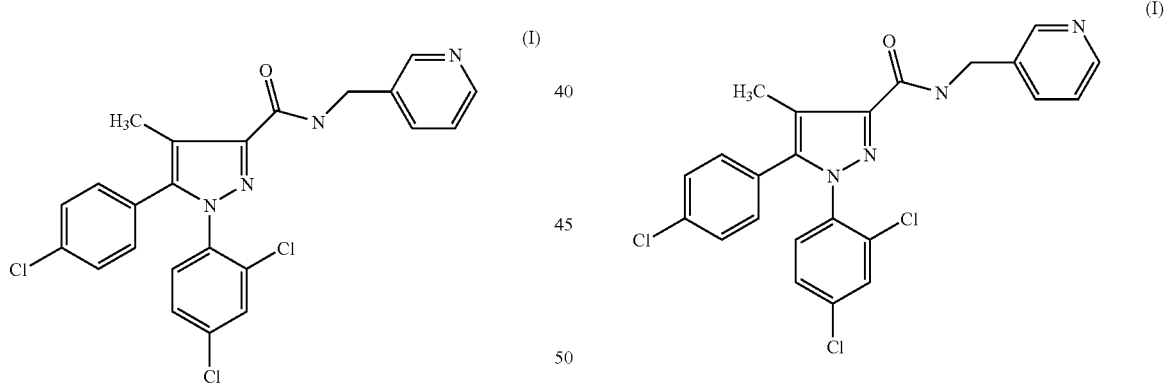

BACKGROUND ART

Cardiovascular disease is resulted by long-term addition of multiple combined dangerous factors, such as smoking, a rise in low-density lipoprotein (LDL), abdominal obesity, decrease in high-density lipoprotein (HDL), high triglyceridemia, hypertension, type II diabetes, and the like. These multiple dangerous factors of cardiovascular disease are closely related to abnormal mode of life, such as unhealthy excessive diet, too little sports and smoking. Recent studies have proofed that endocannabinoid EC system is related to the multiple dangerous factors of cardiovascular disease.

Endocannabinoid EC system is a physiological system in body. It acts on nervous centralis and peripheral tissue and plays a role in regulating body weight, affecting glycolipid metabolism and smoking habituation.

Endocannabinoid EC is an endoagonist of its receptor, it produces on cell membrane based on demand, its metabolism changes rapidly, and usually exerts only at the location where endocannabinoid EC produces. The stimulation of obesity and nicotine causes excessive activation of endocannabinoid EC system, leading to appetite excitation and smoking dependence in nucleus accumbens, promoting increase in intake of food, causing smoking habitation. The stimulation of obesity and nicotine also leads to fatty accumulation in peripheral fatty tissue, and thereby initiating resistance to insulin, damage of carbohydrate tolerance, decrease in adiponectin and high density lipoprotein, and increase of triglyceride.

Studies show that selective cannabinoid CBI receptor antagonists (J. Med. Chem., 2002, 45, 2708-2719) can remarkably reduce body weight and fatty accumulation, improve insulin sensitivity, result in normal blood sugar on an empty stomach, improve lipid, and increase level of adiponectin.

SUMMARY OF THE INVENTION

The purpose of the invention is to provide an antagonist having high affinity to selective cannabinoid CBI receptor of new structure for controlling and reducing an animal or human body weight, decreasing fatty accumulation, nicotine dependence and smoking habitation, improving insulin sensitivity, and resulting in normal blood sugar on an empty stomach.

The present invention provides pyrazole carboxamide derivatives of general formula (I), geometrical isomers thereof, pharmaceutically acceptable salts and/or solvates or hydrates thereof:

According to the present invention, the pharmaceutically acceptable salts of the compound of the present invention include inorganic or organic acid salts. The present invention relates to all forms of these salts, especially acid addition salts formed by association of basic nitrogen atom on pyridine ring of the compound of general formula (I) with acid radical, which include but are not limited to: hydrochlorides, hydrobromides, hydriodides, nitrates, sulfates, hydrosulfates, phosphates, hydrophosphates, acetates, propionates, butyrates, oxalates, trimethyl acetates, adipates, alginates, lactates, citrates, tartrates, succinates, maleates, fumarates, picrates, aspartates, gluconates, benzoates, methanesulfonates, ethanesulfonates, benzenesulfonates, p-toluenesulfonates, salts of pamoic acid, and the like.

Another aspect of the present invention relates to a process for preparing a compound of general formula I or pharmaceutically acceptable salts or hydrates thereof. The compound of the present invention can be prepared via following reaction schemes:

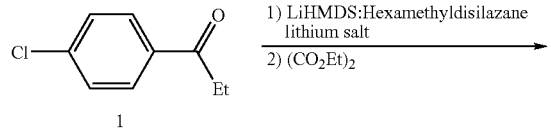

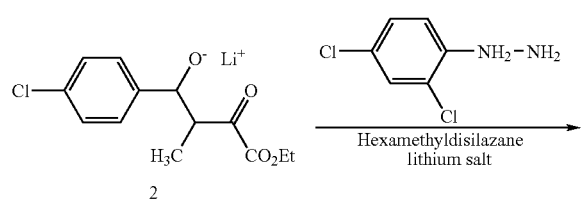

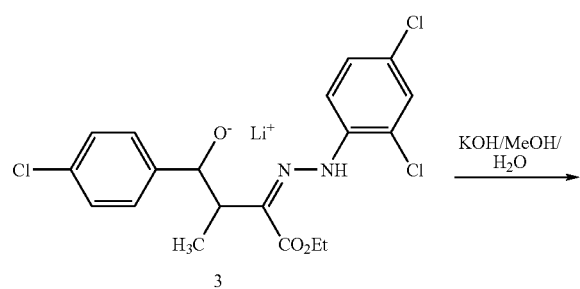

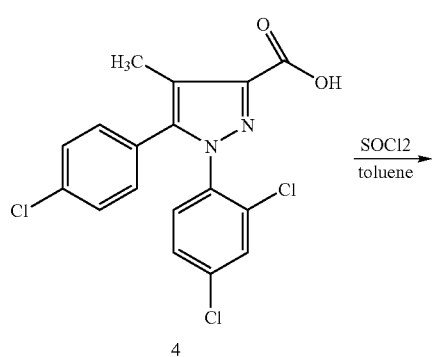

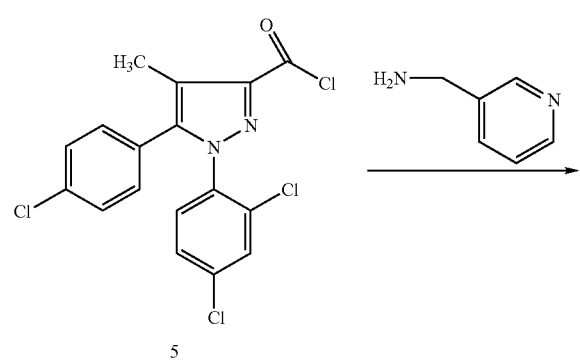

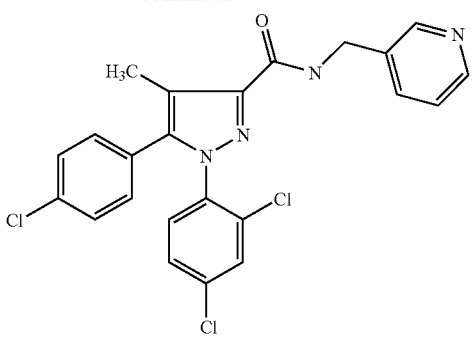

In above reaction schemes, the starting materials 4-chlorophenyl ethyl ketone, hexamethyldisilazane lithium salt, 2,4-dichlorophenylhydrazine, 3-(aminomethyl)-pyridine are commercially available agents from Sigma Company.

In particular,

Step 1: Preparation of Intermediate (2)

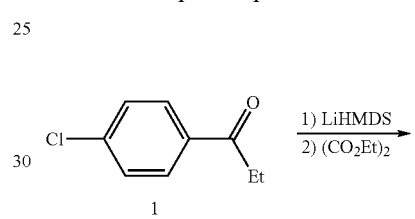

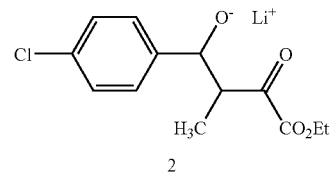

Under nitrogen atmosphere, hexamethyldisilazane lithium salt is dissolved in solvent such as methylcyclohexane or tetrahydrofuran, slowly added dropwise 4-chlorophenyl ethyl ketone at low temperature, upon the completion of the addition, stirred until the white flock disappears and the solution is clear for about 1-2 hours, added diethyl oxalate, the mixture is stirred at room temperature for 20-30 hours, the resultant solid is filtered and collected, dried in vacuum to give a yellow intermediate (2);

Step 2: Preparation of Intermediate (3)

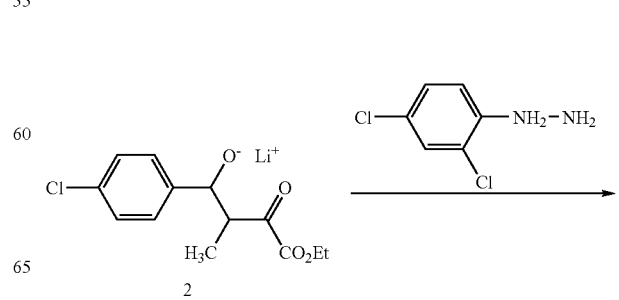

-continued

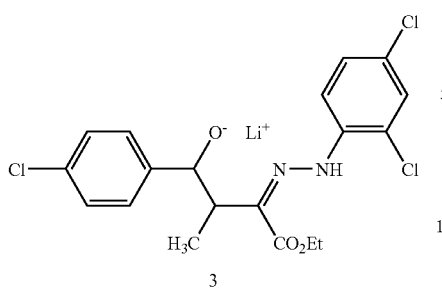

3

Under nitrogen atmosphere, the intermediate (2) and 2,4-dichlorophenyl hydrazine hydrochloride are added to an alcohol solution such as ethanol, the mixture is stirred at room temperature for 2-4 hours, and continuously stirred at room temperature for 48 hours. The precipitate is filtered and collected, washed with ethanol and dried in vacuum to give a yellow solid intermediate (3);

Step 3: Preparation of Intermediate (4)

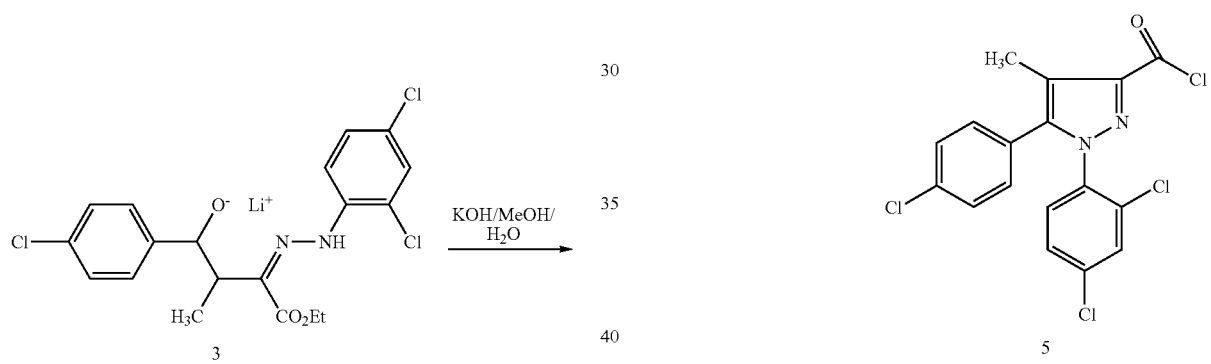

The intermediate (3) is added to an alcohol solution of a base, heated and refluxed for 3 hours, the solution is titrated with an acid to acidity, such as pH of 1. A white flock is precipitated, filtrated, and dried in vacuum to give an intermediate (4);

Step 4: Preparation of Intermediate (5)

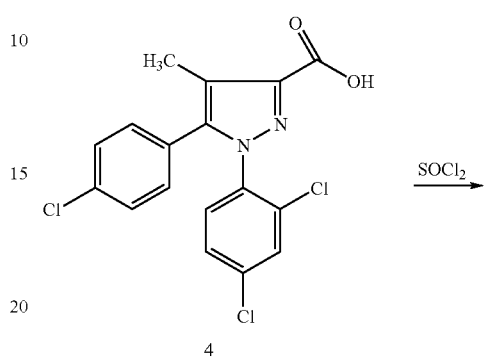

Dichlorosulfoxide is added to toluene solution of the intermediate (4), the mixture is refluxed for 3-4 hours, evaporated in vacuum to dryness to give a yellow solid intermediate (5);

Step 5: Preparation of N-(3-aminomethyl-pyridyl)-5-(4-chlorophenyl)-1-(2,4-dichlorophenyl)-4-methylpyrazol-3-carboxamide

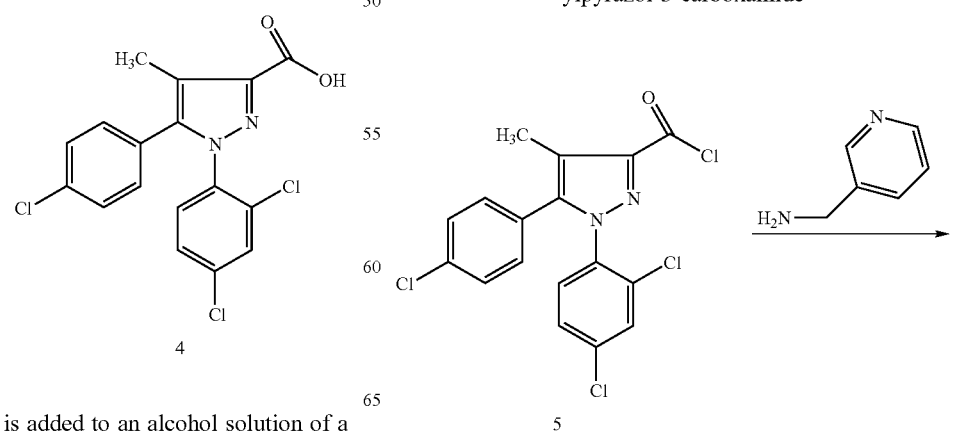

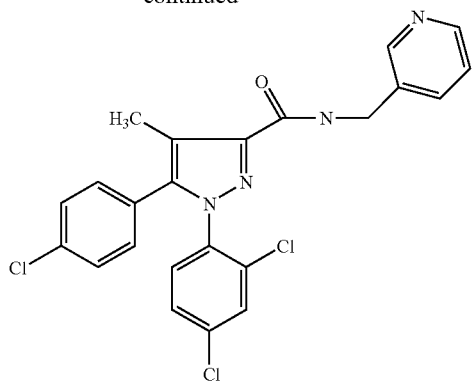

The intermediate (5) is dissolved in methane dichloride, added dropwise to triethylamine solution of 3-(aminomethyl)-pyridine, the mixture is heated to room temperature, stirred for 7-10 hours, separated by column chromatography with petroleum ether:ethyl acetate=1:2 as eluant to give N-(3-aminomethyl-pyridyl)-5-(4-chlorophenyl)-1-(2,4-dichlorophenyl)-4-methy lpyrazol-3-carboxamide as a yellow powder.

According to the present invention, the compound of formula (I) can transmit blood-brain barrier, and thereby has high bioavailability. At meantime, the compound of formula (I) also exhibits advantageous stability in solid and solution, especially stability in aqueous solution. This advantageous stability in solution provides superiority for preparing its oral preparations effectively and on industrialized large scale.

Further, the salt compounds of general formula (I) have excellent workability, they are stable crystalline substances having high melting point. Their solid is loose and has good fluidity, and thus is suitable for preparation and treatment on industrialized large scale, especially pharmaceutical process which needs heat or produces heat, for instance, grinding, heat drying, fluidized bed drying, spray drying and sterilizing at high temperature and high pressure. Therefore, the compound having a structure of general formula (I) can be produced by effective, economic and convenient processes, especially suitable for the production on industrialized large scale.

The present invention further relates to a pharmaceutical composition comprising a compound of general formula (I) and pharmaceutically acceptable salts thereof and/or pharmaceutically acceptable solvates or hydrates thereof and a pharmaceutically acceptable carrier. The pharmaceutical composition can be administered by a plurality of paths, for instance, orally tablets, capsules, powders, oral solutions, injections and transdermal preparations. In accordance with the usual practice of conventional pharmaceuticals, the pharmaceutically acceptable carriers include diluents, fillers, disintegrating agents, wetting agents, lubricants, coloring agents, flavoring agents or other conventional additives. Typical pharmaceutically acceptable carriers include, e.g. avicel, starch, cross-linked povidone, povidone, polyvinylpyrrolidone, maltol, citric acid, sodium lauryl sulfonate or magnesium stearate.

According to the present invention, the compound of general formula (I) and pharmaceutically acceptable salts thereof and/or pharmaceutically acceptable solvates or hydrates thereof exhibit excellent stability in solution, especially in aqueous solution.

The pharmaceutical composition according to the present invention is preferably oral dosage form, wherein unit dosage form usually contains 0.1-1000 mg, preferably 1-500 mg, of a compound of general formula (I) and pharmaceutically acceptable salts thereof and/or pharmaceutically acceptable solvates or hydrates thereof. The composition is administered once or more per day.

More particularly, the compound of general formula (I) N-(3-aminomethyl-pyridyl)-5-(4-chlorophenyl)-1-(2,4-dichlorophenyl)-4-methyl pyrazol-3-carboxamide is an antagonist having high affinity to CBI receptor, its antagonistic concentration of 50% ($EC_{50}$) is $1.3 \times 10^{-10}$ mole.

Thereby, the present invention provides use of a compound of general formula (I) and pharmaceutically acceptable salts thereof and/or pharmaceutically acceptable solvates or hydrates thereof for the preparation of a medicament for preventing or treating diseases or conditions associated with excessive activation of CBI receptor. Said diseases or conditions include but are not limited to controlling and reducing animal or human body weight, reducing fatty accumulation, reducing nicotine dependence, treating smoking habitation, improving insulin sensitivity, and resulting in normal blood sugar on an empty stomach.

Following examples are used for illustrating the present invention, but do not limit the present invention in any way. $^{1}$H NMR spectrum of the compound is determined by ARX-400 NMR. The mass spectrum of the compound is determined by VG-ZabSpec MS. Unless specified otherwise, all reaction solvents are subjected to standardization pretreatment.

EXAMPLE 1

1.1 Preparation of Preparation of Intermediate (2)

Under nitrogen atmosphere, 625 ml of 0.9-1M tetrahydrofuran solution of hexamethyldisilazane lithium salt was added to 2500 ml of ethyl ether. The mixture was cooled to −78° C., added a solution of 105 g of 4-chlorophenyl ethyl ketone in 500 ml ether, stirred for 45 minutes, added rapidly 96 ml diethyl oxalate, the mixture was stirred for 16 hours, heated to room temperature. The resultant precipitate was filtered and collected, washed with ethyl ether, dried in vacuum to give 85 g of intermediate (2).

1.2 Preparation of Intermediate (3)

In nitrogen atmosphere 17 g of 2,4-dichlorophenyl hydrazine hydrochloride was added to 120 ml ethanol solution of the intermediate (2), the mixture was stirred for 16 hours. The reaction solution was placed in ethyl acetate, the precipitate was filtrated, washed with ethyl ether, and refluxed in ethanol for 0.5 hours to give 9 g of fibrillar solid of pale yellow.

1.3 Preparation of Intermediate (4)

8 g of the intermediate (3) was added to 100 ml of 1.1 mol/L ethanol solution of NaOH, the solution became red in color, heat refluxed, the solution changed from red color to black color, and gradually became a transparent solution in pale yellow color, heat refluxed for 3 hours, placed in 200 ml ice water, titrated with HCl solution until pH was 1 to give white flock, filtrated, dried in vacuum to give 6.7 g of intermediate (4).

1.4 Preparation of Intermediate (5)

3.8 ml dichlorosulfoxide was added to a suspension of 6.7 g of the intermediate (4) in 70 ml toluene, the mixture was refluxed for 3 hours, evaporated in vacuum to dryness. The residue was dissolved in 70 ml toluene, and evaporated in vacuum to dryness, such evaporation was repeated for three times to give 6.2 g of yellow solid intermediate (5).

1.5 Preparation of N-(3-aminomethyl-pyridyl)-5-(4-chlorophenyl)-1-2,4-dichlorophenyl)-4-methylpyrazol-3-carboxamide 4 g of the intermediate (5) was dissolved in methane dichloride, added dropwise to the methane dichloride of 2.1 g of 3-(aminomethyl)-pyridine and 2.3 ml triethylamine which was cooled to 0° C. The mixture was heated to room temperature, stirred for 7 hours, separated by column chromatography with petroleum ether:ethyl acetate=1:2 as eluant to give 2.5 g of a yellow powder N-(3-aminomethyl-pyridyl)-5-(4-chlorophenyl)-1-(2,4-dichlorophenyl)-4-methyl pyrazol-3-carboxamide, with a melting point of 178° C.-180° C.

FAB-MS (m/e): 471.1 [M+]; $^1$H NMR(DMSO, δppm): 9.00(s, 1H), 8.55(s, 1H), 8.45(s, 1H), 7.76(m, 3H), 7.48(dd, 1H), 7.45(m, 2H), 7.25(m, 1H), 7.23(m, 2H), 4.42(d, 2H), 2.25(s, 3H).

EXAMPLE 2

Determination of Affinity of N-(3-aminomethyl-pyridyl)-5-(4-chlorophenyl)-1-(2,4-dichlorophenyl)-4-methylpyrazol-3-carboxamide to CB1 Receptor 2.1 Preparation of CB1 receptor membrane protein in cerebellum of rat: Wistar rat, 220-260 g, female and male being not limited, was killed by cutting head, its cerebellum was separated rapidly, weighted and added to a buffer of Tris-HCl in 10 times of volume (50 mM, Tris HCl, 5 mM $MgCl_2.6H_2O$, 1 mM EDTA, 0.5% (W/V) BSA, pH 7.4), homogenized by using homogenizer at 15000 rpm/min, 30 seconds once, 5 times in total. The homogenized liquid was centrifuged at 400×g for 10 minutes, the supernatant was centrifuged at 39000×g for 10 minutes, the precipitate was collected, resuspended with Tris-HCl buffer of pH 7.4 in 10 times of volume of the original weight, and centrifuged at 39000×g for 10 minutes, the precipitate was washed with the same buffer, and centrifuged at 39000×g for 10 minutes, the resultant precipitate was washed with Tris-HCl. The content of CB1 protein was standardized.

2.2 Drug and CB1 Receptor Competition Binding Experiments

100 μg of receptor protein, 20 μl of the compound in Example 1 in mole concentration of $1\times10^{-7}$, $1\times10^{-8}$, $1\times10^{-9}$, $1\times10^{-10}$ and $1\times10^{-11}$, respectively were added successively, reacted at 30° C. for 1 hour, the sample was spotted on glass fiber filtration membrane, filtrated under negative pressure, washed with cold buffer for 10 times, 2 ml per time, the filtration membrane was unwatered, dried over oven, and placed in scintillation bottle, added 1 ml scintillating liquid, the radioactivity strength was detected by LS6500 scintillation counter. The antagonistic concentration of N-(3-aminomethyl-pyridyl)-5-(4-chlorophenyl)-1-(2,4-dichlorophenyl)-4-methylpyrazol-3-carboxamide to CB1 receptor of 50% ($EC_{50}$) was $1.3\times10^{-10}$ mole.

The invention claimed is:

1. A compound of general formula (I) or a pharmaceutically acceptable salt thereof

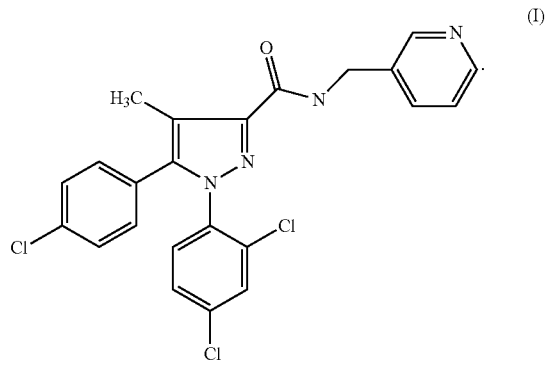

(I)

2. A pharmaceutical composition comprising a compound of general formula (I) according to claim 1 and a pharmaceutically acceptable carrier or an excipient.

* * * * *